United States Patent [19]

Cech et al.

[11] Patent Number: 5,180,818
[45] Date of Patent: Jan. 19, 1993

[54] SITE SPECIFIC CLEAVAGE OF SINGLE-STRANDED DNA

[75] Inventors: Thomas R. Cech; Daniel Herschlag, both of Boulder, Colo.

[73] Assignee: The University of Colorado Foundation, Inc., Boulder, Colo.

[21] Appl. No.: 496,852

[22] Filed: Mar. 21, 1990

[51] Int. Cl.$^5$ .................. C12N 9/00; C12N 15/00
[52] U.S. Cl. .................. 536/23.1; 536/26.26; 435/172.3; 435/193; 435/194
[58] Field of Search ............... 536/27, 28, 29; 435/91, 435/199, 173, 172.3

[56] References Cited

U.S. PATENT DOCUMENTS

| | | | |
|---|---|---|---|
| 4,987,071 | 1/1991 | Cech et al. | 536/27 |
| 5,037,746 | 8/1991 | Cech et al. | 536/27 |
| 5,093,246 | 3/1992 | Cech et al. | 435/91 |

FOREIGN PATENT DOCUMENTS 8804300 6/1988 PCT Int'l Appl. .
8905852 6/1989 PCT Int'l Appl. .

OTHER PUBLICATIONS

Zaug and Cech, 231 Science 470, 1986.
Cech, 236 Science 1532, 1987.
Sugimoto et al., 17 Nucleic Acids Research, 355, 368, 1989.
Haseloff and Gerlach, 334 Nature 585, 1988.
Been and Cech, 47 Cell 207, 1986.
Lambowitz, 56 Cell 323, 1989.
Peebles et al., 44 Cell 213, 1986.
Van der Veen et al., 44 Cell 225, 1986.
Jarrell et al., 263 J. Biol. Chem. 3432, 1988.
Altman, Advances in Enzymology and related areas of Molecular Biology 1, 1989.
Murphy and Cech, 86 Proc. Natl. Acad. Sci. USA 9218-9222, 1989.
Zaug et al., 27 Bioc. 8924, 1988.
van Mansfeld et al., Nature Vo. 288, Dec. 11, 1980.
Woodson and Cech, Cell, vol. 57, 335-345, Apr. 21, 1989.
Zaug et al., Nature, vol. 301, Feb. 1983, pp. 578-583.
Corey and Schulz, 238 Science 1401, 1987.
Corey et al., 28 Biochemistry 8277, 1989.
Szybalski, 40 Gene 169, 1985.
Podhajska and Szybalski, 40 Gene 175, 1985.

*Primary Examiner*—Johnnie R. Brown
*Assistant Examiner*—J. Oliver Wilson
*Attorney, Agent, or Firm*—Lyon & Lyon

[57] ABSTRACT

Method for specifically cleaving a single stranded DNA molecule. The method includes providing an RNA molecule having a deoxyribonuclease activity independent of any protein, and contacting that RNA molecule with the single stranded DNA molecule to cause the single stranded DNA molecule to be cleaved.

8 Claims, 3 Drawing Sheets

SITE SPECIFIC CLEAVAGE OF SINGLE-STRANDED DNA

This invention was made with support from a grant from the National Institute of Health (Grant No. GM 28039). The U.S. Government has rights in the invention.

BACKGROUND OF THE INVENTION

This invention relates to methods for cleaving single-stranded deoxyribonucleic acid (DNA).

Zaug and Cech, 231 Science 470, 1986, state that certain ribonucleic acid (RNA) molecules, now called ribozymes, are able to catalyze cleavage and rejoining of single-stranded RNA molecules. This activity appears to be specific for ribonucleotides; no reaction is observed with deoxyribonucleotides. A chain of five deoxyribocytosine residues ($dC_5$), however, is a competitive inhibitor of cleavage of a chain of five cytosine residues ($C_5$).

Cech, 236 Science 1532, 1987, describes cleavage of mixed oligonucleotides (containing both ribo- and deoxyribo-nucleotides), but only cleavage between a deoxyribonucleotide and a ribonucleotide is observed. No cleavage is observed between two deoxyribonucleotide residues.

Sugimoto et al., 17 Nucleic Acids Research, 355, 368, 1989, describe a reaction where a circular RNA molecule is opened by addition of a dinucleotide, which may include one or more deoxynucleotides. The dinucleotide is added to the RNA molecule, and the circle opened to form a single fragment. No cleavage of DNA is described.

SUMMARY OF THE INVENTION

The invention features a method for specifically cleaving a single-stranded DNA molecule. The method includes providing an RNA molecule (or ribozyme) having a deoxyribonuclease activity independent of any protein, and contacting that RNA molecule with the single-stranded DNA molecule to cause the single-stranded DNA molecule to be cleaved. In this method, a linear DNA molecule is cleaved to form two or more DNA fragments, and a circular DNA molecule is cleaved to form one or more DNA fragments. These fragments are released from the ribozyme as free molecules.

By "specifically cleaving" is meant that the RNA molecule is active at one or only a few short nucleotide sequences of a single-stranded DNA molecule. Such sequences have a length between three and eight deoxynucleotides, generally about four to six deoxynucleotides. The specific sequence that is cleaved can be chosen by altering a portion of the active site of the RNA molecule, a well known procedure described, for example, by Cech et al., PCT application W088/04300; Haseloff and Gerlach, 334 Nature 585, 1988; Been and Cech, 47 Cell 207, 1986; and Haseloff et al., PCT Application W089/05852. A single-stranded DNA molecule includes any molecule having a contiguous sequence of at least four, preferably eight, deoxynucleotides. Such molecules may be bonded with other DNA or RNA molecules, or hybrids thereof.

In preferred embodiments, the method includes providing the RNA molecule in a reaction medium at a concentration sufficient to cause cleavage of at least 1% of a population of the DNA molecules in an hour, most preferably at a concentration sufficient to cause cleavage of at least 10% of such DNA molecules. The reaction medium generally includes DNA molecules at any desired concentration, e.g., between 0.1 nM and 10 $\mu$M, and is maintained at a pH between 6.0 and 9.5, and at a temperature between 20° C. and 70° C. The RNA molecule is generally provided at a concentration between 0.1 $\mu$M and 100 $\mu$M.

The RNA molecule is preferably one that cleaves an RNA molecule to leave a 3'-hydroxyl group; most preferably the RNA molecule includes the deoxyribonuclease cleaving active site of an RNA molecule chosen from a group I or group II intron (Lambowitz, 56 Cell 323, 1989; Peebles et al., 44 Cell 213, 1986; Van der Veen et al., 44 Cell 225, 1986; and Jarrell et al., 263 J. Biol. Chem. 3432, 1988), or RNase P (Altman, Advances in Enzymology and related areas of Molecular Biology, 1, 1989), or derivatives thereof. Even more preferably, the RNA molecule is a derivative of an intervening sequence (IVS) of Tetrahymena, e.g., *T. thermophila*, and the RNA molecule is L-19, L-21, or a derivative thereof.

By "derivative" is meant any RNA molecule which has the active site of any known ribozyme which has a deoxyribonuclease activity. This active site may be altered to specifically cleave a desired single-stranded DNA sequence. Such an RNA molecule need only contain those essential portions of the ribozyme necessary for the deoxyribonuclease activity. Such ribozymes can be readily designed by those of ordinary skill in the art by use of any number of standard techniques.

In other preferred embodiments, the contacting step further includes providing magnesium ions providing guanosine, guanosine monophosphate, guanosine diphosphate or guanosine triphosphate or another guanosine containing moiety, e.g., a dinucleotide containing guanosine; and treating the DNA molecule with a denaturant, e.g., glyoxylate or glyoxal, prior to the contacting step; and the method further includes providing a chelator of magnesium ions, e.g., EDTA, to stop further reaction of the RNA molecule with the DNA molecule.

In yet other preferred embodiments, the RNA molecule includes a binding site for single-stranded DNA which is complementary to a cleavage site on the single stranded DNA molecule; the method includes providing a plurality of RNA molecules, each having a different binding site for single-stranded DNA; and the method further includes separating the cleaved DNA fragments by electrophoresis within a gel matrix.

This invention provides a method by which single-stranded DNA molecules can be specifically cleaved. Such a method is useful because it allows the mapping of specific cleavage sites or nucleotide sequences within DNA. Prior methods for determination of specific DNA sites included digestion of double-stranded DNA with restriction endonucleases. Such restriction endonucleases are active at specific sequences, but their specificity cannot be readily altered. In addition, there are many DNA sequences which no restriction endonuclease is known to cleave. In contrast, ribozymes can be readily altered or synthesized to cleave any desired single-stranded DNA sequence, and thus can be used to characterize DNA molecules with only few limitations on the sites that are recognized.

Although the method is limited to cleavage of single-stranded DNA, double-stranded DNA can be used in the method if it is first denatured to form single-stranded DNA. This method is extremely useful in vitro for genome mapping of humans or other organisms. In addition, the ribozymes can be used in vivo to cleave single-stranded DNA. For example, ribozymes having high activity for cleavage of single-stranded DNA can be used to cleave single-stranded DNA viruses, and thus reduce their infectivity and any disease symptom that they cause.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

RIBOZYMES

Figure 1:
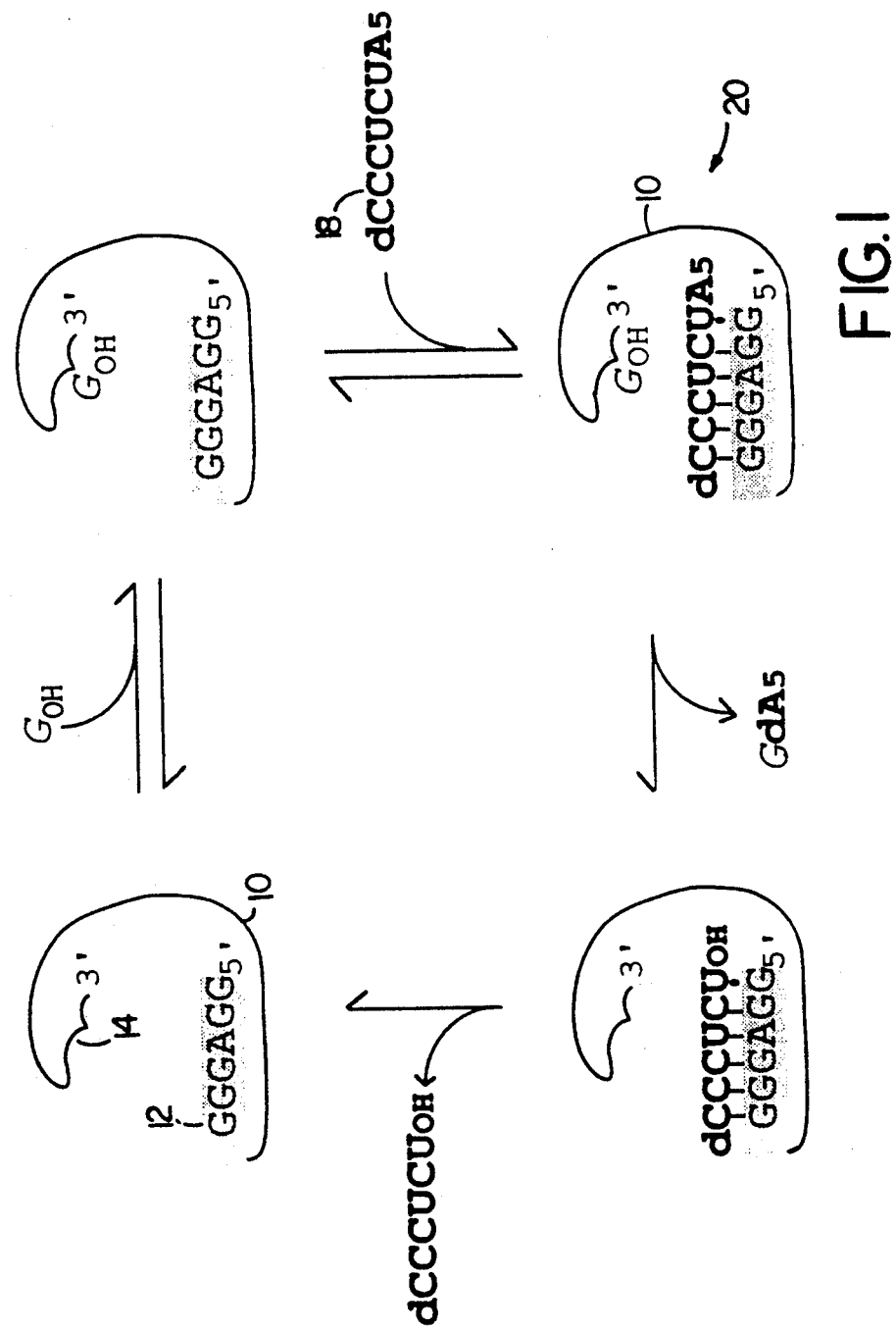
FIG. 1 is a diagrammatic representation of a proposed deoxyribonuclease reaction of a ribozyme.

As discussed above, any ribozyme having deoxyribonuclease activity may be used in this invention. Generally, useful ribozymes are those that cleave an RNA molecule to leave a 3'-hydroxyl group, or a 3' phosphate, and not a 2', 3' cyclic phosphate. These ribozymes can be isolated, and modified to provide derivatives, as described by Cech et al., PCT, supra; Lambowitz, supra, and Van der Veen, supra. Any of a broad group of derivatives of naturally-occurring ribozymes are useful in this invention, all of which can be readily isolated by those of ordinary skill in the art. For example, as described by Cech et al., PCT, supra, the ribozyme of *Tetrahymena thermophilla* can be readily modified so that its active site is active to cleave RNA molecules of different RNA sequence. In a similar manner, this ribozyme can be altered to cleave DNA molecules having differing DNA sequence. Such alterations can be performed by site-directed mutagenesis, or equivalent procedure (see, e.g., Murphy and Cech, Proc. Nat. Acad. Sci. USA., 1990). Generally, the active site is constructed to have a base sequence complementary to the base sequence to be cleaved; that is, at least 3 of 4 bases are positioned to form base pairs, e.g., A is complementary to, and will base pair with, T or U, and G is complementary to, and will base pair with, C or U (where A, T, U, C and G are the standard symbols for adenine, thymine, uracil, cytosine and quanine respectively). In addition, deletion or addition of various portions of the ribozyme, or mutation by other means, can be used to create smaller or larger ribozymes which retain, and preferably increase, their deoxyribonuclease activity. Such alterations are within the ordinary skill of one in the art, and no undue experimentation is required to determine which of those ribozymes are active. Such ribozymes need merely be created and tested in a DNA cleavage protocol, for example, as described below, to determine whether or not they have sufficient deoxyribonuclease activity to be useful in this invention.

Generally, ribozymes useful in this invention are those which can be provided at a concentration in a reaction medium sufficient to cause at least 1%, preferably 10% or more, of a population of DNA molecules to be cleaved within an hour, under the conditions described below. The ratio of the concentration of ribozyme to the concentration of DNA can be varied dependent upon the ribozyme and the DNA and can be in any desired ratio, generally it is between $1:10^6$ and $1000:1$, preferably between 1:10 and 1000:1. The higher the ratio of ribozyme to DNA the faster the reaction will proceed. Higher ratios, however, are wasteful of the ribozyme and need not be used. It is important that the ribozyme used be designed such that the single-stranded DNA substrate is cleaved into one, two or more fragments, which are released from the ribozyme. It is also important that the ribozyme not be altered by the process so that it can recycle and cleave additional DNA molecules.

For in vivo use, it is desirable to have ribozymes that have higher deoxyribonuclease activity under the conditions prevailing in vivo. To this end, ribozymes having an activity to cleave at least 10% of a population of DNA molecules within an hour at 37° C. are desirable.

Although alteration of a synthetic version of an RNA occurring naturally in *Tetrahymena thermophila* is described above, this example is not limiting in the invention since those of ordinary skill in the art can readily alter other group I or group II ribozymes, or RNase P to provide ribozymes useful in this invention.

There follow examples of the use of ribozymes in vitro for cleavage of single-stranded DNA. These examples are not limiting to the invention, are provided merely to illustrate the invention, and those skilled in the art will readily recognize that the invention can be practiced as broadly claimed below.

Referring to FIG. 1, applicants propose a general model for the cleavage of single-stranded DNA by a ribozyme. This model is meant only to illustrate applicant's present understanding of the reaction, and is not meant to be limiting to the invention. This example relates specifically to the deoxyribonuclease activity of a synthetic RNA version of a RNA in *Tetrahymena thermophila* ribozyme; this synthetic version is a ribozyme. In FIG. 1, the deoxyribonuclease reaction of the L-21 ScaI ribozyme (Zaug et al., 27 Bioc. 8924, 1988) with a DNA substrate 18 (deoxy-CCCUCUA$_5$) is shown. All of the steps are reversible. The binding of guanosine (G) prior to oligonucleotide substrate 18 is shown for simplicity; the two binding sites (substrate and G binding sites) are essentially independent so that either order of addition can occur. The 5' sequence of the ribozyme (shaded, GGGAGG-5'), called the 5' exon-binding site 12, is responsible for recognition of the substrate by base pairing.

Referring again to FIG. 1, it is proposed that ribozyme 10 has a substrate binding site 12, and a guanosine binding site 14. A guanosine residue (G) binds to site 14. Active site 12 of the ribozyme then interacts with a substrate 18 to form the structure shown as 20. Ribozyme 10 in structure 20 causes cleavage of substrate 18 to release a deoxy A$_5$ chain having the guanosine residue attached (GdA$_5$), and the remainder of the substrate (dCCCUCU$_{OH}$), to reform ribozyme 10. Thus, ribozyme 10 acts in a catalytic manner since it is able to act on any number of substrates to cause cleavage of each substrate and subsequent release of the fragments resulting from the cleavage.

L-21 ScaI of T. thermophila

Figure 2:
FIGS. 2 and 3 are photographs of polyacrylamide gels demonstrating the deoxyribonuclease activity of a ribozyme (in FIG. 2 the lanes are referred to below as lanes 1–8 starting from the left hand side)

Referring to FIG. 2, there is shown the results of the deoxynucleotide cleavage reaction of a DNA oligonucleotide substrate catalyzed by the ribozyme L-21 ScaI. The ribozyme was formed by standard procedure (Zaug et al., 27 Bioc. 8924, 1988). The substrate, deoxy-CCCUCUA$_5$, was provided at a concentration of approximately 2 nanomolar and labeled at its 5'-end with $^{32}$P. It was synthesized on an Applied Biosciences DNA synthesizer. This substrate was incubated at a concentration of 2 nanomolar with 1 micromolar L-21 ScaI ribozyme (id.) for 15 hours at 50° C. in the presence of 800 micromolar G, 50 millimolar MES (buffer), pH 7.0, and 10 millimolar MgCl$_2$ (lane 4). The same reaction was performed without G (lane 5), with 800 micromolar ATP replacing the G (lane 6), without MgCl$_2$ (lane 7), and without ribozyme (lane 8). Lane 2 shows the substrate alone, and lane 3 shows the putative product, deoxy $^{32}$P-CCCUCU. Lane 1 shows the products from digestion of the substrate by 0.2 units per microliter P1 nuclease in 1 millimolar Tris, pH 7.5, 2 millimolar zinc chloride, 0.1 millimolar EDTA, and 0.1 microgram per microliter tRNA for 60 minutes at 37° C.

Ribozyme reactions were initiated by addition of the DNA substrate after a 10 minute preincubation of the ribozyme, buffer, and MgCl$_2$ at 50° C. Reactions were quenched with EDTA and urea at 0° C. and subjected to electrophoresis on the 20% denaturing polyacrylamide gel, as described by Zaug et al., id.

The DNA substrate was specifically cleaved at the same position as the analogous RNA substrate for this ribozyme. A single labelled product is formed from this DNA substrate. This product comigrates with deoxy $^{32}$P-CCCUCU (lane 3) and with the appropriate product from P1 nuclease digestion of the DNA substrate (lane 1). Mg$^{2+}$ is required (lane 7). ATP (adenosine triphosphate) cannot substitute for G (lane 6), and GTP (guanosine triphosphate) can substitute for G (not shown), each of which is also a property of the reaction with RNA substrates. A small amount of product is formed in the absence of added G (lanes 5 and 6, seen in longer exposures). This is analogous to the slow hydrolysis of RNA substrates that occurs in the absence of G. Similar experiments with deoxy-$^{32}$P-CCCUCUA also gave specific cleavage between U and A dependent on the presence of the ribozyme.

Figure 3:
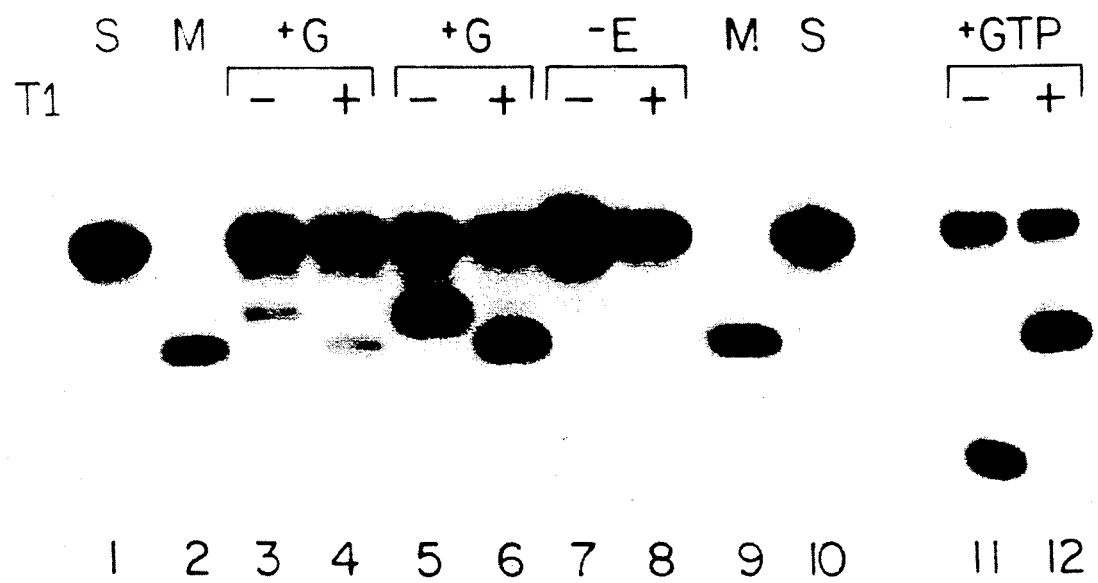

Referring to FIG. 3, using DNA substrate that was 3'-end labeled, it was demonstrated that the guanosine cofactor was covalently added to the 3'-product fragment. Deoxy-CCCUCUA$_5$ $^{32}$P-3'dA (2 nM, produced by reaction of deoxy-CCCUCUA$_5$ with [α-$^{32}$P]3'dATP in the presence of terminal transferase) was incubated for four hours with 4 μM L-21 ScaI ribozyme, 50 mM MES, pH 7.0, and 10 or 100 mM MgCl$_2$. One aliquot was quenched with EDTA and urea (shown as "−" in FIG. 3), the other was treated with 0.05 U/μl ribonuclease T1 for 1 hour at 37° C. (shown as "+" in FIG. 3). Lanes 3 and 4 show reaction with 1 mM G and 10 mM MgCl$_2$; lanes 5 and 6 show reaction with 1 μM G and 100 mM MgCl$_2$; lanes 11 and 12 show reaction with 1 mM GTP and 100 mM MgCl$_2$ (reaction is faster with higher MgCl$_2$ concentrations); lanes 7 and 8 are from incubation with 1 mM GTP and 100 mM MgCl$_2$ in the absence of ribozyme; lanes 1 and 10 show substrate alone; and lanes 2 and 9 show deoxy-A$_5$ $^{32}$P-3'dA(M). The product from reaction of deoxy-CCCUCUA$_5$p$^{32}$P-3'dA with GTP (lane 11) migrated faster in a polyacrylamide gel than the product from reaction with G (lanes 3 and 5, conditions as above; no products were observed without a guanosine cofactor, without MgCl$_2$, or without ribozyme). The products from the ribozyme reactions with GTP and with G (lanes 4, 6 and 12) comigrated following treatment by ribonuclease T1, which cleaves after (ribo)-guanosine residues that have 3'-phosphoryl groups. The new product formed from T1 treatment comigrated with $_{HO}$dA$_5$$^{32}$P3'dA$_{OH}$ (lanes 2 and 9), as expected from the mechanism outlined in FIG. 1.

The DNA endonuclease reaction is catalytic. For example, a reaction mixture with 25 μM DNA substrate (deoxy-CCCUCUA$_5$) and a trace (about 1 nM) of 5'-end-labeled substrate was incubated with 0.55 μM ribozyme and 800 μM G for 20 hours. Five percent of the labeled DNA was converted to product, which corresponds to more than two turnovers.

Figure 4:
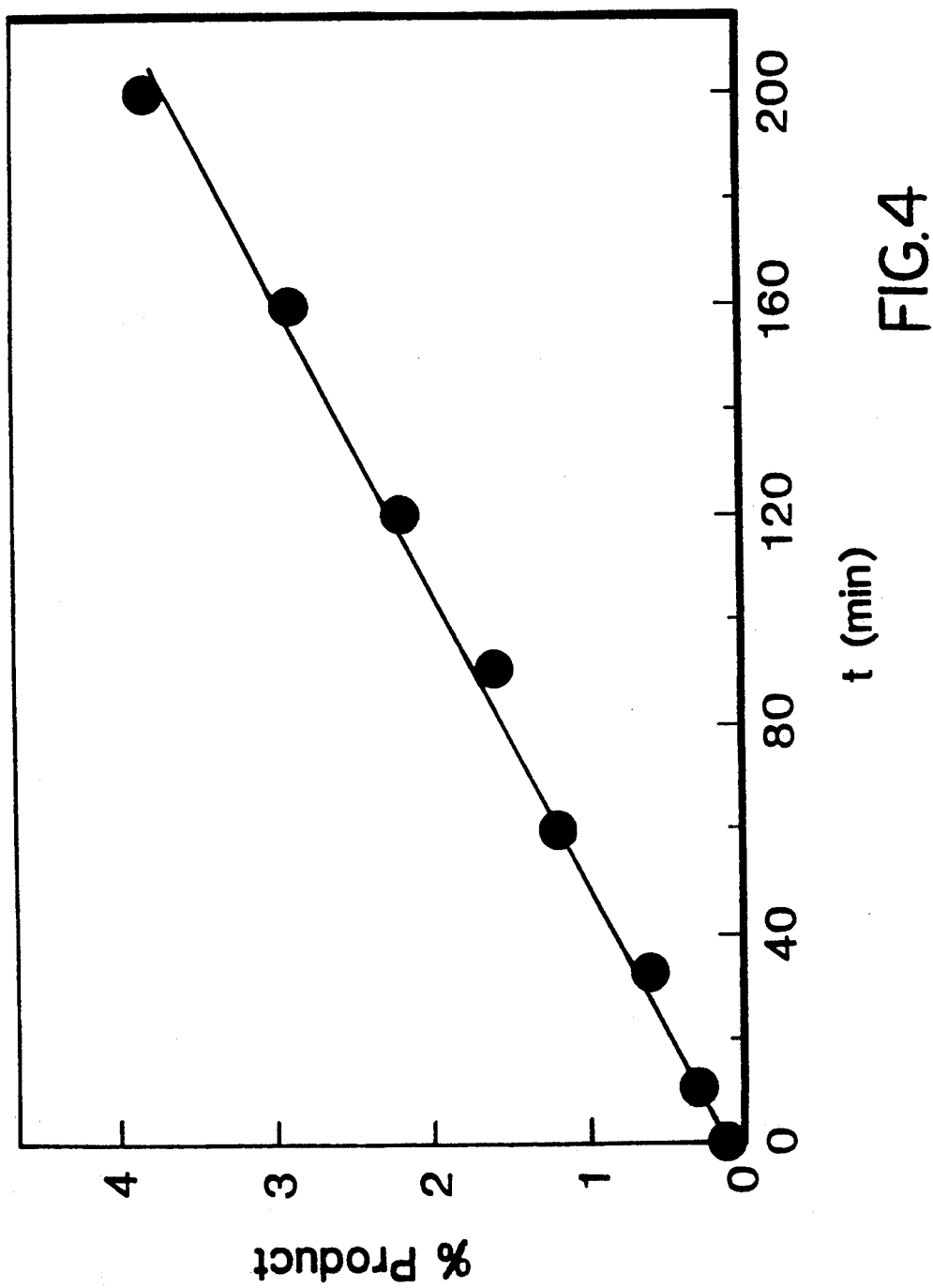
FIG. 4 is a graphical representation of the time course for reaction of a ribozyme with a single-stranded DNA substrate.

Referring to FIG. 4, there is shown a time course for formation of product (deoxy $^{32}$P-CCCUCU) from deoxy $^{32}$P-CCCUCUA$_5$ (2 nM) with 1.1 micromolar ribozyme, 800 micromolar G, 50 millimolar MES, pH 7, and 10 millimolar MgCl$_2$ at 50° C. The reactions were quenched, products separated by denaturing gel electrophoresis, and quantitated with an AMBIS radioanalytical scanner. As can be seen from the graph, approximately 1% of product is released every 30–50 minutes under these conditions.

DNA substrates have a lower affinity and a slower rate of reaction than a corresponding RNA substrate with a ribozyme. Lengthening of the internal guide sequence will improve binding, and may increase the rate of DNA endonuclease reaction.

USES

As discussed above, the method of this invention is useful for determining the location of specific DNA sequences in a single-stranded DNA molecule. Such analysis is analagous to restriction endonuclease mapping, using restriction endonuclease proteins and double-stranded DNA. Generally, double stranded DNA is denatured, and the single-stranded DNA molecules resulting from the denaturation, contacted with a ribozyme under appropriate conditions (e.g., those described above) to produce one, two or more single-stranded DNA fragments which can then be separated in a gel matrix. The size of the resulting fragments reflects the position of the specific DNA site in the single-stranded DNA molecule.

Separate aliquots of the DNA may be treated with different ribozymes so that the location of different cleavage sites can be determined. In some experiments it may be useful to contact the DNA with two, or even more, ribozymes; or the DNA may be contacted with one ribozyme and after removing the first ribozyme, contacted with a second ribozyme.

The method of this invention can be used in vivo by contacting single-stranded DNA, within a cell or in medium surrounding the cell, with a ribozyme that is active under in vivo conditions. Alternatively, the ribozyme may be synthesized in vivo by transfection of a DNA molecule into a cell in a manner that causes expression of that DNA molecule to produce the desired ribozyme in vivo. That ribozyme may then be active to cleave any single-stranded DNA within the cell.

Other embodiments are within the following claims.
We claim:

1. A method for specifically cleaving a single-stranded DNA molecule, comprising the steps of:
   (a) providing a first RNA molecule selected from the group consisting of a group I intron, a group II intron, or RNAse P, that cleaves a second RNA molecule to leave a 3'-OH, said first RNA molecule having a deoxyribonuclease activity, and
   (b) contacting said first RNA molecule with said single-stranded DNA molecule under conditions which allow said first RNA molecule to cause said single-stranded DNA molecule to be cleaved said conditions including providing $Mg^{2+}$ ions and guanosine or guanosine triphosphate at a pH between 6.0 and 9.5 and a temperature between 20° C. and 70° C.

2. The method of claim 1, further comprising providing said RNA molecule in a reaction medium at a concentration sufficient to cause cleavage of at least 1% of a population of the DNA molecules in an hour.

3. The method of claim 1, further comprising providing said RNA molecule in a reaction medium at a concentration sufficient to cause cleavage of at least 10% of a population of the DNA molecules in an hour.

4. The method of claim 1, wherein said RNA molecule comprises the portions of an RNA molecule of Tetrahymena having said deoxyribonuclease activity.

5. The method of claim 4, wherein said RNA molecule is L-19, L-21, or an RNA molecule comprising the portions of L-19 having said deoxyribonuclease activity.

6. The method of claim 1, further comprising the step of providing a chelator of said $Mg^{2+}$ ions to stop further reaction of said RNA molecule with said DNA molecule.

7. The method of claim 6, wherein said chelator is ethylenediaminetetraacetic acid (EDTA).

8. The method of claim 1, wherein said RNA molecule comprises a binding site for single-stranded DNA, which binding site is complementary to nucleotides adjacent to a cleavage site on said single-stranded DNA molecule.

* * * * *

UNITED STATES PATENT AND TRADEMARK OFFICE
CERTIFICATE OF CORRECTION

PATENT NO. : 5,180,818
DATED : January 19, 1993
INVENTOR(S) : Cech, Thomas R. et al.

It is certified that error appears in the above-indentified patent and that said Letters Patent is hereby corrected as shown below:

Column 3, Line 40: delete "thermophilla", replace with --thermophila"

Column 7, Line 17: insert --first-- between "said and "RNA"

Column 7, Line 21: insert --first-- between "said" and "RNA"

Column 8, line 3: insert --first-- between "said" and "RNA"

Column 8, line 6: insert --first-- between "said" and "RNA"

Column 8, line 13: insert --first-- between "said" and "RNA"

Column 8, Line 16: insert --first-- between "said" and "RNA"

Signed and Sealed this

Twenty-third Day of August, 1994

Attest:

BRUCE LEHMAN

*Attesting Officer*  *Commissioner of Patents and Trademarks*